United States Patent [19]
Holleman et al.

[11] Patent Number: 5,115,818
[45] Date of Patent: May 26, 1992

[54] IMPLANTABLE ELECTRODE

[75] Inventors: Timothy W. Holleman, Ham Lake; Sandra F. Viktora, Coon Rapids, both of Minn.

[73] Assignee: Medtronic, Inc., Minneapolis, Minn.

[21] Appl. No.: 639,632

[22] Filed: Jan. 10, 1991

Related U.S. Application Data

[62] Division of Ser. No. 479,928, Feb. 14, 1990, Pat. No. 5,042,143.

[51] Int. Cl.⁵ .............................................. A61N 1/05
[52] U.S. Cl. ...................... 128/784; 128/786
[58] Field of Search ............ 128/784, 786, 419 P, 128/419 D

[56] References Cited

U.S. PATENT DOCUMENTS

| | | | |
|---|---|---|---|
| 4,154,246 | 5/1979 | LeVeen | 128/786 |
| 4,161,952 | 7/1979 | Kinney et al. | 128/786 |
| 4,817,634 | 4/1989 | Holleman et al. | 128/784 |
| 4,860,769 | 8/1989 | Fogarty et al. | 128/786 |
| 4,934,049 | 6/1990 | Kiekhafer et al. | 128/784 |

Primary Examiner—Lee S. Cohen
Attorney, Agent, or Firm—Reed A. Duthler; Harold R. Patton

[57] ABSTRACT

An implantable electrode of the type in which an elongated wire coil forms the electrode surface. The electrode coil is mounted around an insulative lead body and is stabilized on the lead body by means of a plastic filler between the individual turns of the electrode coil, extending radially outward to approximately one-third of the diameter of the electrode coil wire. The filler is produced by stretching a portion of the lead body which normally displays an outer diameter greater than the inner diameter of the electrode coil, sliding the electrode coil over the lead body and inserting a mandral into the lead body to urge the lead body into contact with the electrode coil. This assembly is heated to encourage flow of the lead body into the spaces between the electrode coil to stabilize the coil on electrode body and to prevent fibrotic ingrowth around the electrode coil wire.

4 Claims, 2 Drawing Sheets

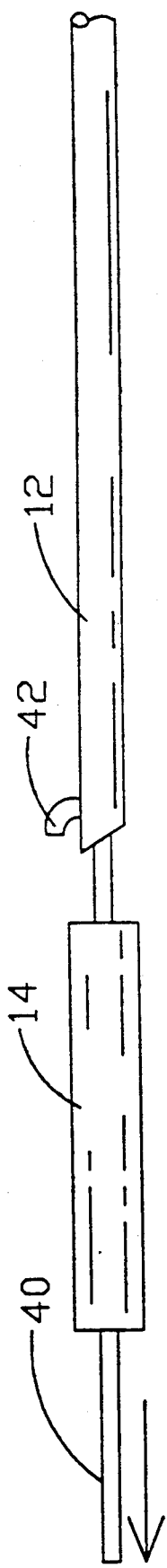
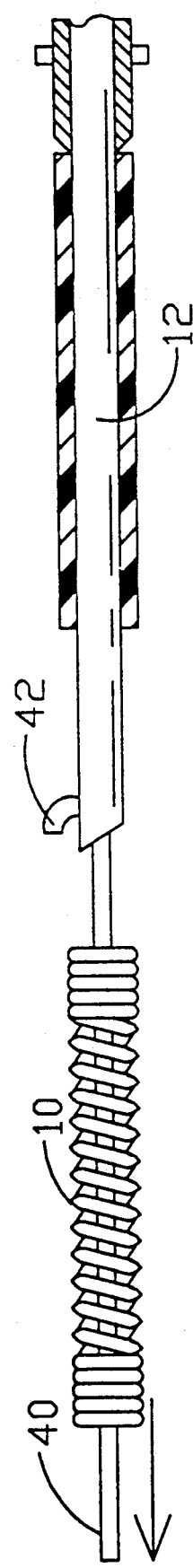
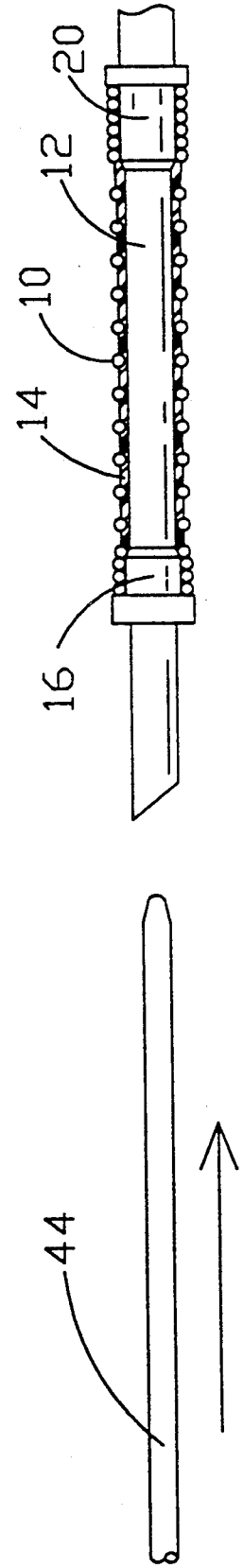

IMPLANTABLE ELECTRODE

This is a divisional of copending application Ser. No. 07/479,928, filed on Feb. 14, 1990, now U.S. Pat. No. 5,042,143.

BACKGROUND OF THE INVENTION

This invention relates to medical electrical stimulation electrodes in general and to defibrillation electrodes in particular.

In the past years, there has been substantial activity toward development of a practical implantable defibrillator. Most proposals involve the use of large surface area implantable electrodes either to be mounted within the heart, on the exterior of the heart or subcutaneously. One common approach of providing a large surface area electrode is to employ an elongated exposed coil of biocompatible metal. In the context of an endocardial lead, this is disclosed in U.S. Pat. No. 4,161,952 issued to Kinney. In the context of an epicardial lead, this is disclosed in the context of U.S. Pat. No. 4,187,634 issued to Holleman et al.

In an endocardial lead, an elongated coil serving as the electrode can be mounted around the exterior of an insulative lead body. It is believed desirable in this context to stabilize the electrode coil with respect to the lead body, both to provide mechanical integrity and to prevent fibrous in growth around the individual coils of the electrode coil. In the above cited Kinney et al patent, this is accomplished by sliding the coil over the lead body and backfilling the spaces between the electrode coil with a plastic material. The exterior surface of the electrode is then machined to provide a smooth surface. Alternatively, the backfilling may be removed by means of a plasma etch as disclosed in commonly assigned, co-pending application Ser. No. 07/376,731 by Kiekhafer et al, for a "Method for Fabrication of a Medical Electrode" filed Jul. 7, 1989, now U.S. Pat. No. 4,934,049. In this application, the backfilling is illustrated as extending radially outward between the turns of the coil about one-third to one-half the diameter of the coil wire. This application is incorporated herein by reference in its entirety.

SUMMARY OF THE INVENTION

The present invention is directed to producing a pacing lead having a structure similar to that of a structure produced by the method disclosed in the above cited Kiekhafer application but without the necessity of the use of a backfilling step which is time consuming and generally involves a large amount of hand labor. The method of the present invention also allows the use of materials which are not readily applied using a backfilling method.

BRIEF DESCRIPTION OF THE DRAWINGS

FIG. 2 illustrates an initial step of the manufacture of the electrode illustrated in FIG. 1;

FIGS. 3 and 4 illustrate various points within the process of assembly of the electrode illustrated in FIG. 1.

DETAILED DESCRIPTION OF THE INVENTION

Figure 1:
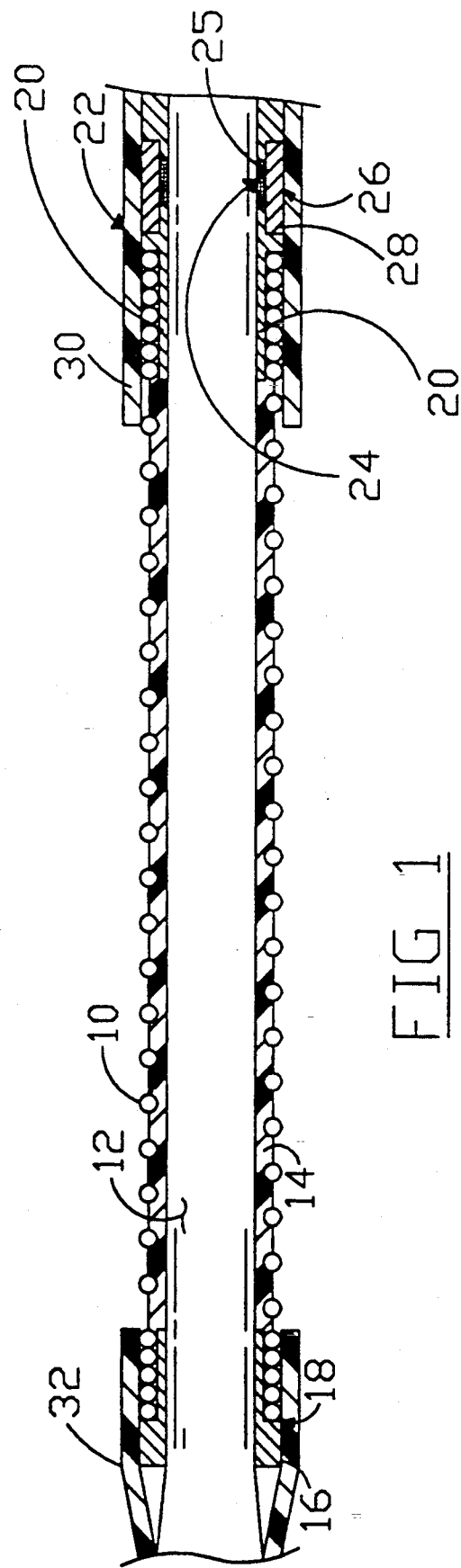
FIG. 1 illustrates a side cutaway view through a defibrillation electrode manufactured according to the present invention.

FIG. 1 is a side cutaway view through an endocardial defibrillation electrode according to the present invention. The electrode coil 10 is a space wound, single filar coil of platinum mounted around insulative tubing 12. Between the coil 10 and the tubing 12 and between the individual turns of the coil 10 is a filler plastic tube 14 which is preferably insulative, but may be conductive plastic in some cases. The filler plastic tube 14 extends radially outward from sheath 12 between the individual turns of coil 10 and typically extends outward between the individual turns of coil 10 to a distance of approximately one-third the diameter of the wire from which coil 10 is fabricated.

Tube 14 and tubing 12 are preferably fabricated of an implantable elastic plastic, preferably a polyurethane. Tube 14 and tubing 12 together form the lead body in the vicinity of electrode coil 10. At its distal end, coil 10 is coupled to a welding sleeve 16 by means of a laser weld at shoulder 18. Similarly at its proximal end, coil 10 is coupled to transition sleeve 20 by means of a laser weld at shoulder 22. Welding sleeve 16 and transitional sleeve 20 are both preferably fabricated of an inert, conductive metal such as platinum to which coil 10 may be readily welded. Transitional sleeve 20 is provided with two perpendicular bores 24 and a circumferential groove 26. A band 28 of insulative material, preferably polyurethane, fills circumferential groove 26, and bores 24 are backfilled with an appropriate adhesive to attach band 28 to tubing 12 assisting in stabilizing the electrode assembly. Transitional sleeve 20 extends proximally into contact with an elongated coiled conductor (not illustrated) extending to the proximal end of the lead. This conductor serves to couple defibrillation electrode 10 to an implantable defibrillator and may be manufactured using any conventional technique known to the art and coupled to transitional sleeve 20 using any conventional technique known to the art such as crimping, welding, etc. Surrounding the proximal portion of electrode coil 10 is an outer insulative sheath 30 which extends proximally to the proximal end of the lead, covering the coil coupled to transitional sleeve 20.

At the distal end of the lead, an outer insulative sheath 32 covers the distal end of electrode coil 10 and may extend distally to one or more pacing electrodes coupled to conductors within tubing 12. In the preferred embodiment of the present invention, outer insulative sheaths 30 and 32 are fabricated of a polyurethane of one of the types typically used in conjunction with cardiac pacing leads and are preferably mechanically coupled to the proximal and distal ends of electrode coil 10 by means of an adhesive to further stabilize their locations.

FIG. 2 illustrates an early step in the manufacture of a defibrillation electrode according to the present invention. In this early step, tube 12 is attached to a holding fixture at its proximal end (not illustrated) and filler tube 14 is slid over a stylet 40. Stylet 40 is provided with a hooked and 42 passed through the distal end of tubing 12.

Preferably tubing 12 displays an outer diameter somewhat greater than the inner diameter of filler tube 14. For example, tubing 12 may be 0.068"×0.082" Pellethane ® 2363-80A polyurethane, and filler tube 14 may be a 0.079"×0.095" tube fabricated of the same material.

Filler tube 14 is placed over stylet 40. The hooked end of stylet 40 is passed through the wall of tubing 12 and used to extend the wall of tubing 12 until the diameter of tubing 12 has decreased sufficiently to slide filler tube 14 over tubing 12. Preferably, approximately 1¼" of tubing 12 extends distal to filler tube 14. Freon may be used to lubricate tubing 12 to facilitate this step, if necessary.

The assembly of tubing 12 and filler tube 14 is then allowed to air dry for approximately ½ hour, and a urethane adhesive is then backfilled between filler tube 14 and tubing 12 at the proximal and distal ends of filler tubing 14.

This assembly is allowed to air dry and is placed in an oven under nigrogen purge. The oven temperature is gradually increased to 150° C. After about five to ten minutes at 150° C., the oven is shut off, and the temperature allowed to fall. This heating step relieves any stresses built up in the tubing. The tubing is removed from the oven and allowed to cool to room temperature.

FIG. 3 illustrates a later step in the assembly process. Prior to this step, the transition sleeve 20 has been located adjacent the proximal end of filler tubing 14. Electrode coil 10, preferably has an inner diameter less than the outer diameter of the assembly comprising tubing 12 and filler tubing 14. Coil 10 may be a space wound coil of platinum wire and may have an inner diameter of 0.092". Coil 10 is placed over stylet 40, and the hooked distal end 42 of stylet 40 is again passed through the distal end of tubing 12. Stylet 40 is used to stretch tubing 12 and filler tube 14, allowing coil 10 to be slid proximally over filler tube 14 until its proximal end abuts the circumferential shoulder 22 of transition sleeve 20. Tubing 12 and tube 14 are the allowed to relax and re-expand into contact with the interior of electrode coil 10.

FIG. 4 illustrates a subsequent step in the process of manufacture of the electrode and shows welding sleeve 16 slipped over tubing 12 inside the distal end of electrode coil 10. At this point, the inner diameter of tubing 12 is less than its normal inner diameter as tubing 12 and filler tube 14 are under radial compression by electrode coil 10. Teflon coated mandral 44 has an outer diameter approximately equal to the inner diameter of tubing 10 in its relaxed, uncompressed state. Mandral 44 is lubricated with alcohol and slid into the interior of tubing 10 compressing tubing 10 and filler tubing 14 against the interior of coil 10. This assembly is allowed to air dry and is then placed into an oven gradually heated to 150° C. under nitrogen purge in order to cause flow of filler tube 14 between the individual turns of electrode coil 10 to produce the structure illustrated in FIG. 1 above. After about five to ten minutes at 150° C., the oven is turned off and the temperature is allowed to gradually fall.

The assembly is then removed from the oven, allowed to cool for at least 30 minutes, and the mandral is removed. Removal of the mandral maybe facilitated by injection of air between the tubing and the mandral. Alternatively, alcohol may be injected between the tubing and the mandral to facilitate removal of the mandral.

Preferably, the relative sizes of tubing 12, filler tubing 14 and electrode coil 10 should be such that after this baking step, material from filler tube 14 extends radially within the spaces between the individual turns electrode coil 10 a distance of approximately one-third to one-half of the diameter of the wire from which electrode coil 10 is fabricated.

The remainder of the assembly of the lead typically follows the completion of this step and would include laser welding of the electrode 10 and two sleeves 16 and 20, coupling of a conductor coil to the proximal end of sleeve 20 and location of outer insulative sheaths 30 and 32 overlapping proximal and distal ends, respectively, of electrode coil 10 as illustrated in FIG. 1. Assembly of the remainder of the lead may also optionally include the provision of one or more pacing electrodes at the distal end of the lead and will include the provision of an electrical connector assembly at the proximal end of the lead. Addition of these assemblies to the lead may be accomplished using any of a number of available prior art structures and manufacturing techniques such as those disclosed in U.S. Pat. No. 4,506,680, U.S. Pat. No. 4,502,492, U.S. Pat. No. 4,258,725, U.S. Pat. No. 4,106,512, or U.S. Pat. Application Ser. No. 07/198,540, filed May 25, 1988 by Doan et al for a "Connector For Multiconductor Leads", all of which are incorporated herein by reference. However, it is believed that one of skill in the art would readily appreciate that the present invention can be applied to any elongated medical electrical lead employing any desired combination of additional electrodes, sensors and connectors.

As such, the embodiment illustrated above should be considered exemplary rather than limiting with regard to the scope of the following claims In conjunction with the above specification, we claim:

1. An implantable electrode lead comprising:
    an elongated polyurethane lead body, an elongated space wound electrode coil fabricated from a conductive wire having a cross-sectional diameter, exposed to the exterior of said polyurethane lead body, said polyurethane lead body extending radially outward between individual turns of said electrode coil to a depth of approximately one-third or greater of said diameter of said wire; and
    conductor means for coupling said electrode coil to an implantable medical device.

2. A lead according to claim 1 wherein said polyurethane lead body extends radially outward between individual turns of said electrode coil to a depth of approximately one-third to one-half of said diameter of said wire.

3. An implantable electrode lead comprising:
    an elongated tubular polyurethane lead body, an elongated space wound electrode coil mounted to the exterior of said polyurethane lead body, wherein said electrode coil is fabricated from a conductive wire having a cross-sectional diameter, said polyurethane lead body extending radially outward between individual turns of said electrode coil to a depth of at least approximately one-third of the diameter of said wire; and
    conductor means for coupling said electrode coil to an implantable medical device.

4. A lead according to claim 3 wherein said polyurethane lead body extends radially outward between individual turns of said electrode coil to a depth of approximately one-third to one-half the diameter of said wire.

* * * * *